United States Patent [19]

Prahl

[11] 4,203,433
[45] May 20, 1980

[54] SPREADING DEVICE FOR TREATMENT OF HIP DYSPLASTIES

[75] Inventor: Gertraud Prahl, Rullstorf, Fed. Rep. of Germany

[73] Assignee: A. Nattermann & Cie. GmbH, Cologne, Fed. Rep. of Germany

[21] Appl. No.: 11,766

[22] Filed: Feb. 12, 1979

[30] Foreign Application Priority Data

Feb. 14, 1978 [DE] Fed. Rep. of Germany ....... 2806173

[51] Int. Cl.² .............................................. A61F 3/00
[52] U.S. Cl. ............................... 128/80 A; 128/87 C
[58] Field of Search ..................... 128/80 A, 87 C, 83

[56] References Cited

U.S. PATENT DOCUMENTS

| | | | |
|---|---|---|---|
| 3,068,862 | 12/1962 | Fuzere | 128/80 A |
| 3,274,997 | 9/1966 | Hewson, Jr. | 128/87 C |
| 3,730,177 | 5/1973 | Thum | 128/80 A |
| 3,815,589 | 6/1974 | Bosley | 128/80 A |

*Primary Examiner*—John D. Yasko
*Attorney, Agent, or Firm*—Burns, Doane, Swecker & Mathis

[57] ABSTRACT

A spreading device for the treatment of hip dysplasties comprises a back support for engagement with a patient's back in the area of the sacrum. From the back support two side portions extend to the front, to each of which a thigh splint in the nature of a leaf spring is connected. The ends of the thigh splints form supporting dishes each to be engaged with a thigh of the patient at or above the ham.

3 Claims, 6 Drawing Figures

SPREADING DEVICE FOR TREATMENT OF HIP DYSPLASTIES

BACKGROUND AND OBJECTS OF THE INVENTION

The invention relates to a spreading device for treatment of hip dysplasties, which device retains the patient's legs in a spread-out condition to retain the parts of the hip in proper relationship.

Hip dysplasties or dysplasties of the hip joints or thigh joints which can be subjected to treatment by means of such devices occur rather frequently with newborn babies. Such dysplasties usually involve too steep a formation of the roof of the socket of the coxa and a discoloration of the globular head of the femur from the center of the socket, without necessarily also presenting luxation or subluxation. Such ill formed hip joints must be subjected to a kind of treatment which will orient the globular head of the femur to the center of the socket and exert axial stimulating pressure to promote the formation of the ball and socket joint. This can be achieved by putting the legs into a spread-out position at which the globular head automatically will be oriented downwards to the center of the socket of the coxa because of the engaging muscles. Treatment by means of a spreading device usually is initiated at an early infant age before the child begins to stand up and walk. It is important that the spreading device should not unduly restrict the child's movements in order not to inhibit the development of the muscles.

In a known spreading device of this kind, back support and side portions are associated with a pelvis basket which has openings for the thighs and the front of which is constituted by a spreader bar with an upwardly directed projection connected by securing means in the area of its top end with the two side portions above the thigh openings. Thigh splints, which are like leaf springs, are each pivotally supported at a side portion above the thigh openings, and in a rest position they enclose an angle of 30° to 40° with the sagittal plane or plane of symmetry of the pelvis basket. Thus, each thigh splint extends parallel to the associated thigh at the outer side thereof. The supporting dishes are mounted at the thigh splints for adjustment in longitudinal direction of the splints and each comprises a belt embracing the thigh.

With such a known spreading device the desired achievement and success of the treatment cannot be obtained unless the following conditions are observed:

(a) The pelvis basket must be applied firmly to the child by a hip belt and by tightening the above-described securing means between the upwardly directed projection of the spreading bar and the two side portions so that the child cannot become displaced laterally in the pelvis basket. Otherwise, the child might adopt a position at which the required spreading is guaranteed for one thigh only, whereas the other thigh could return almost to normal position.

(b) The supporting dishes must be so adjusted that they exactly reach the hams or knee hollows, and the corresponding belts must be placed tightly around the thighs. Otherwise the child might attempt to close the thighs and thus press the globular heads of both hip joints outwardly again towards the upper edge of the socket thereby causing a mechanical load distribution which is unfavorable for the success of the treatment. Usually the infant patient finds these conditions annoying after a short while so that he is tempted to get rid of at least part of the belts surrounding his thighs and body, and larger children soon are successful in thus freeing themselves. This presents another hazard for successful treatment.

The known pelvis basket also is an obstacle to the proper personal hygiene of the child.

It is, therefore, an object of the invention to provide an improved spreading device of this type which will guarantee that both a spread-out position and stressing of the thighs which are favorable for successful treatment are maintained while, at the same time, obstructing and annoying the patient as little as possible.

It is another object of the invention to provide such a spreading device which is uncomplicated and easy to install.

It is a further object of the invention to provide such a spreading device that promotes personal hygiene of the patient.

It is yet another object of the invention to provide such a spreading device which an infant patient cannot remove.

These objects are met, in accordance with the invention, in that the thigh splints are joined to the associated side portions by arches, each of which extend forwardly towards the inside and is to be applied to the patient between the pelvis and the thigh. The thigh splints are to be applied diagonally to the inner sides of the thighs, from the top in front to the bottom towards the rear. The spreading device is designed as a spreading brace of the general nature of a leaf spring, leaving free the zone of the patient's perineum and rump.

This makes it possible for a forwardly directed supporting force to act on the sacrum and, furthermore, for pressure from above to be exerted on the femoral neck areas and pressure from below to be exerted simultaneously on the thighs in the area of the hams, while the legs are in spread-off or spread-out position. Thereby, the globular head of the femur of each coxa is oriented towards the center of the corresponding socket without the use of any belt tightened around the thigh or body. As the design of the spreading braces according to the invention is such as to resemble a leaf spring, the three points of support defined above are interconnected flexibly so that the required corrective pressure is exerted at each of them, with the patient in any position. The infant patient is uncovered at body parts which may become dirty, and he can wear any of the commercially available diaper panties. Furthermore, he is also free to make any movements corresponding to his age without risking a displacement of the spreading braces which would endanger the success of the treatment.

Preferably the spreading brace in accordance with the invention is formed integrally of plastics, various copolymers having proved to be especially well suited.

In a preferred embodiment of the invention the longitudinal axes of the thigh splints, in relaxed condition, lie at least approximately in a common plane at right angles to the plane of symmetry of the spreading device.

The spreading braces thus formed according to the invention are applied to the patient from behind so that the back support will abut in the area of the sacrum. From that area the two side portions extend into the areas of the thighs, and each arch joined to the side portions extends between the pelvis and the thigh to the front side of the thigh. Then the corresponding thigh splint extends across the front and inner sides of the thigh, diagonally into the ham, where the lower part of the thigh is embraced by the associated supporting dish upon having introduced the thigh from behind into the supporting dish by lever action. The child thus is unable to strip off the spreading brace according to the invention without any help from outside.

BRIEF DESCRIPTION OF THE DRAWINGS

A preferred embodiment of the invention will be described in more detail below, with reference to the accompanying diagrammatic drawings, in which.

DETAILED DESCRIPTION OF A PREFERRED OBJECT OF THE INVENTION

Figure 1:
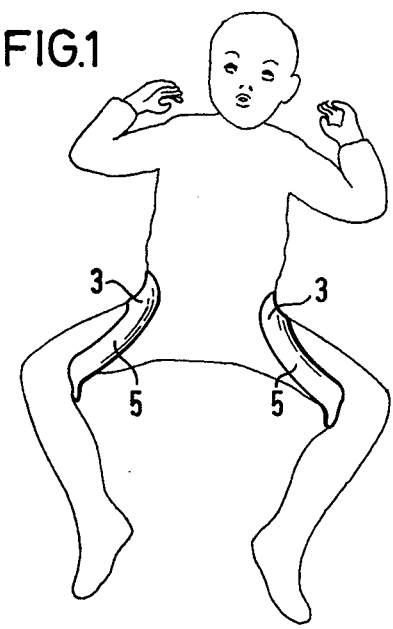
FIG. 1 shows a child wearing a spreading brace according to the invention and lying on its back.
Figure 2:
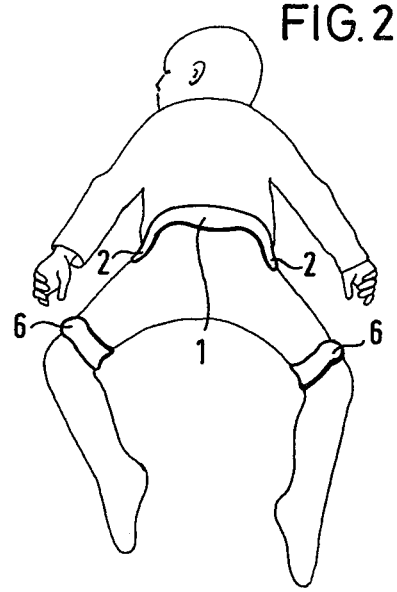
FIG. 2 shows the child lying on its stomach.

A brace or spreading device according to the present invention comprises a wide back support 1 from which two side portions 2 extend to the front. Each side portion merges into a bow portion or an arch 3 gripping across the corresponding thigh in spread-out position, in the fold between the pelvis and the thigh so as to exert downwardly directed pressure, as marked by the arrow 4, on the hip joint or coxa. Each arch is resiliently flexibly joined to a thigh splint 5 in the manner of a leaf spring. Each thigh splint extends in smooth arcuate shape diagonally across the inner side of the corresponding thigh up to the middle thereof and then straight to the ham. The end of each thigh splint 5 is shaped as a supporting dish 6 which, in the installed condition, exerts pressure in an upward direction on the thigh, as shown by the arrow 7.

Figure 3:
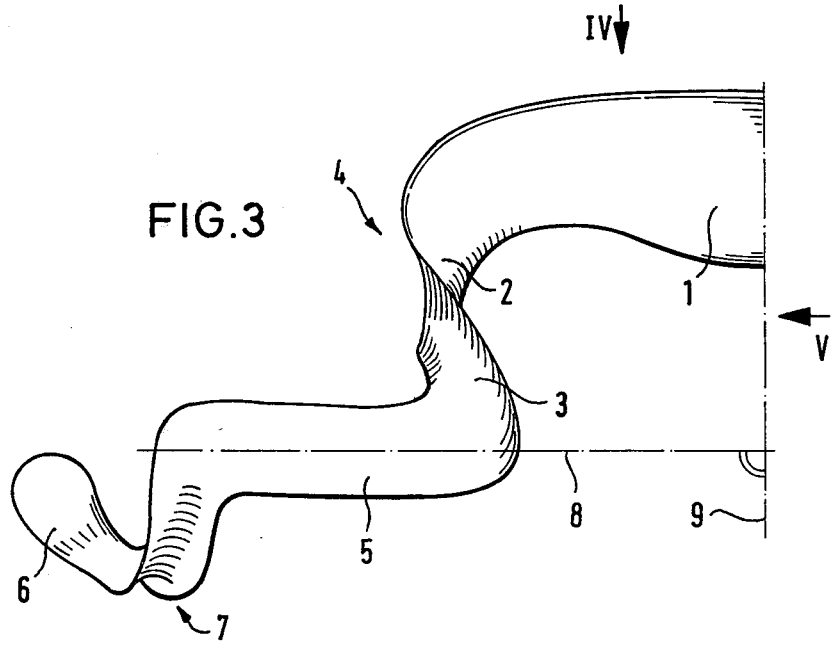
FIG. 3 shows a front view of one half of the spreading braces in relaxed condition on an enlarged scale.
Figure 4:
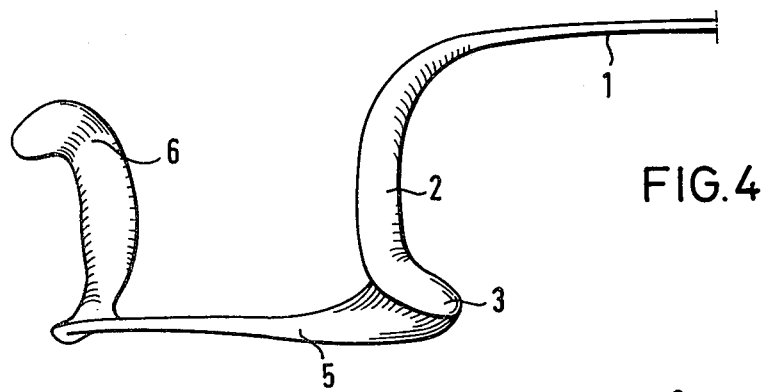
FIG. 4 shows a plan view of said one half of the spreading braces as seen in the direction of arrow IV in FIG. 3
Figure 5:
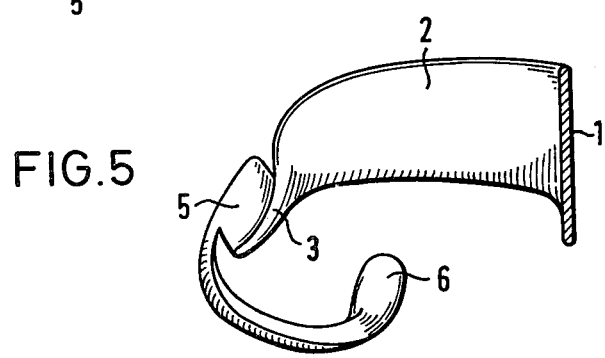
FIG. 5 shows an end view as seen in the direction of arrow V in FIG. 3.
Figure 6:
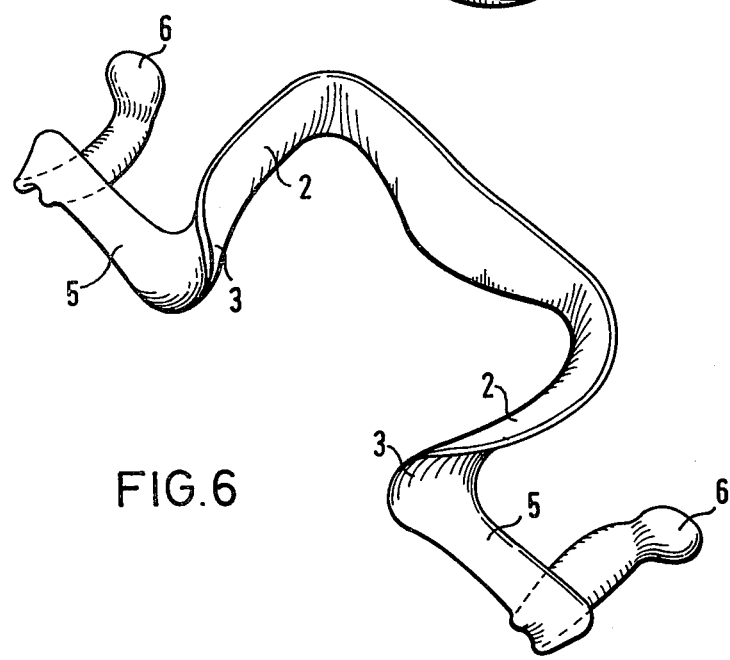
FIG. 6 shows a perspective view of the spreading braces in their entirety.

In relaxed condition of the spreading braces (FIG. 3) according to the invention the longitudinal axes 8 of the thigh splints 5 lie in a plane perpendicular to the plane of symmetry 9 of the spreading braces, as may be viewed in FIG. 3. In this condition the supporting dishes 6 are in a position in which their open side is facing upwards.

The spreading brace is preferably formed of one-piece integral construction of plastics. Various copolymers such as acryl-butadiene-styrene have been found to be especially well suited.

To install the spreader, the back support 1 is positioned to engage the patient's back in the area of the sacrum. The arches 3 are fixed slightly apart so as to accommodate the entry of the patient. The thigh splints are flexed downwardly to enable the patient's legs to be inserted such that each ham is positioned within the supported disk portions 6 of the thigh splints, with the thigh splints extending diagonally across the front and inner sides of the thigh. Upon release, the thigh splints 5 tend to spring upwardly, thereby imposing upward pressure 7 on the thighs in the area of the hams. Simultaneously, the arches 3 impose downward pressure 4 on the hip joint or coxa and, more particularly, on the femoral neck areas. At the same time, a forwardly directed force is exerted on the sacrum by the back support 1.

Accordingly, the globular head of the femur of each coxa is oriented toward the center of the corresponding socket. This is achieved without the need for a belt tightened around the thigh or trunk.

It will be appreciated that the back support 1, arches 3, and thigh splints 5 are flexibly connected to form a leaf spring type of arrangement which exerts the necessary forces with the patient in any position. The infant patient is uncovered at body parts which may become soiled, and thus can be easily cleaned. Also, the infant can wear the commercially available diapers. In addition, the infant patient is free to make movements typical of an infant without risking a displacement of the spreading thighs such as to endanger the success of the treatment.

Although the invention has been described in connection with a perferred embodiment thereof, it will be appreciated by those skilled in the art that additions, modifications, substitutions and deletions not specifically described may be made without departing from the spirit and scope of the invention as defined in the appended claims.

What is claimed is:

1. A spreading device for the treatment of hip dysplasties, comprising
    a back support portion for engagement with a patient's back in the area of the sacrum,
    a pair of side portions extending forwardly from said back portion along opposite sides of the patient,
    a pair of arch portions joined to the forward ends of said side portions, said arch portions extending forwardly and inwardly and arranged for engagement between the pelvis and thigh of the patient, and
    a pair of thigh splint portions each resiliently flexibly connected to a forward end of one of said arch portions in the manner of a leaf spring, said thigh splints arranged for engagement diagonally with inner sides of the thighs from an upper front portion to a lower rear portion of each thigh, leaving open and unobstructed the general area of the patient's perineum and rump,
    the lower end of each thigh splint including a generally dish-shaped support for engagement with a thigh of the patient at or above the ham.

2. A spreading device according to claim 1 wherein said back support portion, side portions, arch portions, and thigh splint portions are of integral one-piece construction, formed of a plastic material.

3. A spreading device according to claim 1, wherein in a relaxed condition the longitudinal axes of the thigh splints lie at least approximately in a common plane perpendicular to the plane of symmetry of the spreading device.

* * * * *